US00PP30341P2

(12) United States Plant Patent
O'Connell

(10) Patent No.: US PP30,341 P2
(45) Date of Patent: Apr. 2, 2019

(54) ***PACHYVERIA* PLANT NAMED 'SPRING BOUQUET'**

(50) Latin Name: *Pachyveria hybrida*
Varietal Denomination: Spring Bouquet

(71) Applicant: Altman Specialty Plants, Inc, Vista, CA (US)

(72) Inventor: Renee O'Connell, Escondido, CA (US)

(73) Assignee: Altman Specialty Plants, Inc, Vista, CA (US)

( * ) Notice: Subject to any disclaimer, the term of this patent is extended or adjusted under 35 U.S.C. 154(b) by 0 days.

(21) Appl. No.: 15/732,286

(22) Filed: Oct. 18, 2017

(51) Int. Cl.
*A01H 5/12* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
(74) *Attorney, Agent, or Firm* — Cassandra Bright

(57) ABSTRACT

A new and distinct *Pachyveria* cultivar named 'Spring Bouquet' is disclosed, characterized by rosettes of terete, fusiform mint green leaves with red tips. The new cultivar is offsets freely, forming an attractive mounding cluster. The new cultivar 'Spring Bouquet' is more resistant to leaf detaching and can be easily reproduced by leaflings. The new variety is a *Pachyveria*, typically produced as container plants for the patio or as landscape plants, as a variety of ornamental purposes.

1 Drawing Sheet

Latin name of the genus and species: *Pachyveria hybrida.*
Variety denomination: 'SPRING BOUQUET'.

BACKGROUND OF THE INVENTION

The new cultivar, *Pachyveria* 'Spring Bouquet', is the product of a planned breeding program. The new variety originated from a cross pollination of the proprietary, unpatented, seed parent, *Echeveria hybrida* 'JJ', with the pollen parent an unpatented, proprietary variety of *Pachyphytum hybrida* known as 'JDA.' The cross pollination was made during February 2013, in Vista, Calif., at a commercial greenhouse. The new cultivar 'SPRING BOUQUET' was discovered by the inventor, Renee O'Connell, in March 2014, in Vista, Calif. at a commercial greenhouse.

Asexual reproduction of the new cultivar 'SPRING BOUQUET' was first performed in Vista, Calif., at a commercial greenhouse, by terminal vegetative cuttings. *Pachyveria* 'SPRING BOUQUET' has since produced multiple generations, also by leaf cuttings, and has shown that the unique features of this cultivar are stable and reproduced true to type.

SUMMARY OF THE INVENTION

The cultivar 'SPRING BOUQUET' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SPRING BOUQUET'. These characteristics in combination distinguish 'SPRING BOUQUET' as a new and distinct *Pachyveria* cultivar:

1. *Pachyveria* 'Spring Bouquet' can be characterized by rosettes of terete, fusiform mint green leaves with red tips, a leaf color combination not observed with most other comparable *Pachyveria* varieties.
2. *Pachyveria* 'Spring Bouquet' offsets freely to produce an attractive mounding cluster, not observed in other comparable *Pachyveria* which usually grow taller, becoming a group of leaves sitting atop a stem.
3. The leaves of *Pachyveria* 'Spring Bouquet' are not easily detached by touching the plant, in contrast to the easily detached leaves of many comparable *Pachyphytums*, which are readily detached by touching the plant.
4. *Pachyveria* 'Spring Bouquet' is very easily reproduced by leaflings, thereby enhancing production in the commercial nursery.
5. *Pachyveria* 'Spring Bouquet', due to its mint green leaves accented by red tips, can be readily utilized in holiday decorations such as centerpieces or bouquets.

PARENTAL COMPARISON

Plants of the new cultivar are similar to plants of the seed parent, in most horticultural characteristics, however, plants of the new cultivar differ in the following;

1. *Pachyveria* 'Spring Bouquet' displays terete, fusiform leaves, whereas *Echeveria* 'JJ' exhibits flatter, somewhat more rounded, longer leaves.
2. *Pachyveria* 'Spring Bouquet' offsets freely to produce mounded clusters, whereas *Echeveria* 'JJ' produces an occasional offset, and slowly forms a cluster.
3. The new cultivar *Pachyveria* 'Spring Bouquet' produces rosettes of mint green leaves, whereas the leaves of *Echeveria* 'JJ' are a darker green, with a reddish blush.
4. *Pachyveria* 'Spring Bouquet' is readily reproduced by leaflings, whereas *Echeveria* 'JJ' does not reproduce as prolifically from leaflings.
5. *Pachyveria* 'Spring Bouquet' grows faster than *Echeveria* 'JJ'.

Plants of the new cultivar are similar to plants of the pollen parent, in most horticultural characteristics, however, plants of the new cultivar differ in the following;

1. *Pachyveria* 'Spring Bouquet' produces mint green leaves with red tips, whereas the pollen parent *Pachyphytum* 'JDA' produces mint green leaves without red tips.
2. *Pachyveria* 'Spring Bouquet' does not grow as fast as *Pachyphytum* 'JDA'.
3. *Pachyveria* 'Spring Bouquet' produces compact clusters of small rosettes, whereas *Pachyphytum* 'JDA' grows taller, producing offsets but not in a compact cluster.
4. *Pachyveria* 'Spring Bouquet' produces a flower that is morphologically intermediate between the typical *Echeveria* flower and a typical *Pachyphytum* flower, whereas *Pachyphytum* 'JDA' produces a typical *Pachyphytum* flower.

COMMERCIAL COMPARISON

The new cultivar 'Spring Bouquet' can be compared to the unpatented commercially known *Pachyveria clavifolia*. Plants of the *Pachyveria clavifolia* are similar to plants of the new cultivar 'Spring Bouquet' in most horticultural characteristics. However, the new cultivar 'Spring Bouquet' differs in the following:

1 *Pachyveria* 'Spring Bouquet' forms mounded clusters to 6" in height and 8" or more in diameter, whereas, this comparator produces groups of multiple stems that are not mounding in morphology.
2. *Pachyveria* 'Spring Bouquet' produces clusters of mint green rosettes, blushed apically red, particularly in cooler weather, whereas *Pachyveria clavifolia* produces stems of blue-green leaves.
3. *Pachyveria* 'Spring Bouquet' is faster growing than *Pachyveria clavifolia* enhancing production time in a commercial nursery.
4. The leaves of *Pachyveria* 'Spring Bouquet' do not easily detach, whereas the leaves of *Pachyveria clavifolia* can be easily detached when touched.

The new cultivar 'Spring Bouquet' can be compared to the unpatented commercial variety *Pachyveria* 'Powder Puff'. Plants of *Pachyveria* 'Powder Puff' are similar to plants of the new cultivar 'Spring Bouquet' in most horticultural characteristics. However, plants of the new cultivar 'Spring Bouquet' differ in the following:

1. *Pachyveria* 'Powder Puff' quickly begins to produce a taller stem, consequently becoming lax and pendant, whereas *Pachyveria* 'Spring Bouquet' forms mounding rosettes.
2. *Pachyveria* 'Spring Bouquet' exhibits mint green leaves, apically blushed reddish, particularly in cooler weather, whereas *Pachyveria* 'Powder Puff' displays pruinose blue leaves.
3. *Pachyveria* 'Spring Bouquet' offsets prolifically, whereas *Pachyveria* 'Powder Puff' produces less branches.

BRIEF DESCRIPTION OF THE PHOTOGRAPH

The accompanying photograph illustrates in full color a typical plant of 'Spring Bouquet' grown in a greenhouse in Vista, Calif. The photograph was taken using conventional techniques and equipment. While the colors in this photograph may display variances of color as compared to the living cultivar, due to LRV (light reflectance value), it is as accurate as possible using conventional photographic techniques. Colors in the photograph may appear to differ slightly from the color values cited in the botanical description, which accurately describe the colors of the new *Pachyveria* plant. The photograph depicts a plant grown under natural light conditions of approximately 4500 foot-candles during early Summer at approximately 6 months of age. Temperatures ranged from about 5° C. to 29° C. night and day. No artificial light, photoperiodic treatments or chemical treatments were given to the plants.

DETAILED BOTANICAL DESCRIPTION

In the following description, color references are made to The Royal Horticultural Society Colour Chart, 2007, except where general terms of ordinary dictionary significance are used. The following observations and measurements describe 'Spring Bouquet' plants in a commercial greenhouse in Vista, Calif. Temperatures ranged from −1° C. to 29° C. night and day. No artificial light, photoperiodic treatments or chemical treatments were given to the plants. Natural light conditions were approximately 2500 to 4000 fc of light. Measurements and numerical values represent averages of typical plant types.

Botanical classification: *Pachyveria hybrida* 'SPRING BOUQUET'.

PROPAGATION

Type of propagation typically used: Terminal vegetative cuttings.

Time to initiate roots: About 11 days at approximately 24° C.

Root description: Fibrous, tan in color, not accurately measured with an R.H.S. chart.

PLANT

Age of plant described: Approximately 4 months from a cutting.

Container size of the plant described: 1 quart.

Growth habit: Densely rosulate, mounding plant.

Height: Approximately 10 cm to top of highest leaf.

Plant spread: Approximately 16.0 cm.

Growth rate: Moderate.

Branching characteristics: Not typically observed.

FOLIAGE

Leaf:

*Arrangement.*—Rosulate.
*Average length.*—3 cm.
*Average width.*—1.0.
*Width at base.*—Average 0.7 cm.
*Thickness of leaf.*—Thickest section, near base 5 mm.
*Shape of blade.*—Spatulate with overall shape slightly claw-like and curving.
*Aspect.*—Slight upward curve.
*Apex.*—Mucronate.
*Base.*—Broad attenuate.
*Margin.*—Entire.
*Texture of top surface.*—Slightly glaucous.
*Texture of bottom surface.*—Slightly glaucous.
*Appearance of top surface.*—Matte.
*Appearance of bottom surface.*—Matte.
*Quantity of leaves per rosette.*—Average range 25 to 40.

*Color*.—Young foliage upper side: Near RHS Green 138C, base near Yellow-Green 145D. Apex slightly Red 53A. Young foliage under side: Near RHS Green 138C, base near Yellow-Green 145D. Apex very slightly Red 53A. Mature foliage upper side: Near RHS Green 138C, base near Yellow-Green 145D. Apex Red 53A. Mature foliage, under side: Near RHS Green 138C, base near Yellow-Green 145D. Apex Red 53A.

FLOWER

Not observed.

REPRODUCTIVE ORGANS

Not observed.

OTHER CHARACTERISTICS

Fruits and seeds: Not observed.

Temperature tolerance: Tolerates temperatures from approximately −2° C. to at least 35° C.

Disease/pest resistance: Neither resistance or susceptibility to normal diseases and pests of *Echeveria* or *Pachyphytum* has been observed.

Drought tolerance: Tolerates at least 3 weeks of high temperatures without supplemental water, showing no serious damage to plant.

What is claimed is:

1. A new and distinct cultivar of *Pachyveria* plant named 'SPRING BOUQUET' as herein illustrated and described.

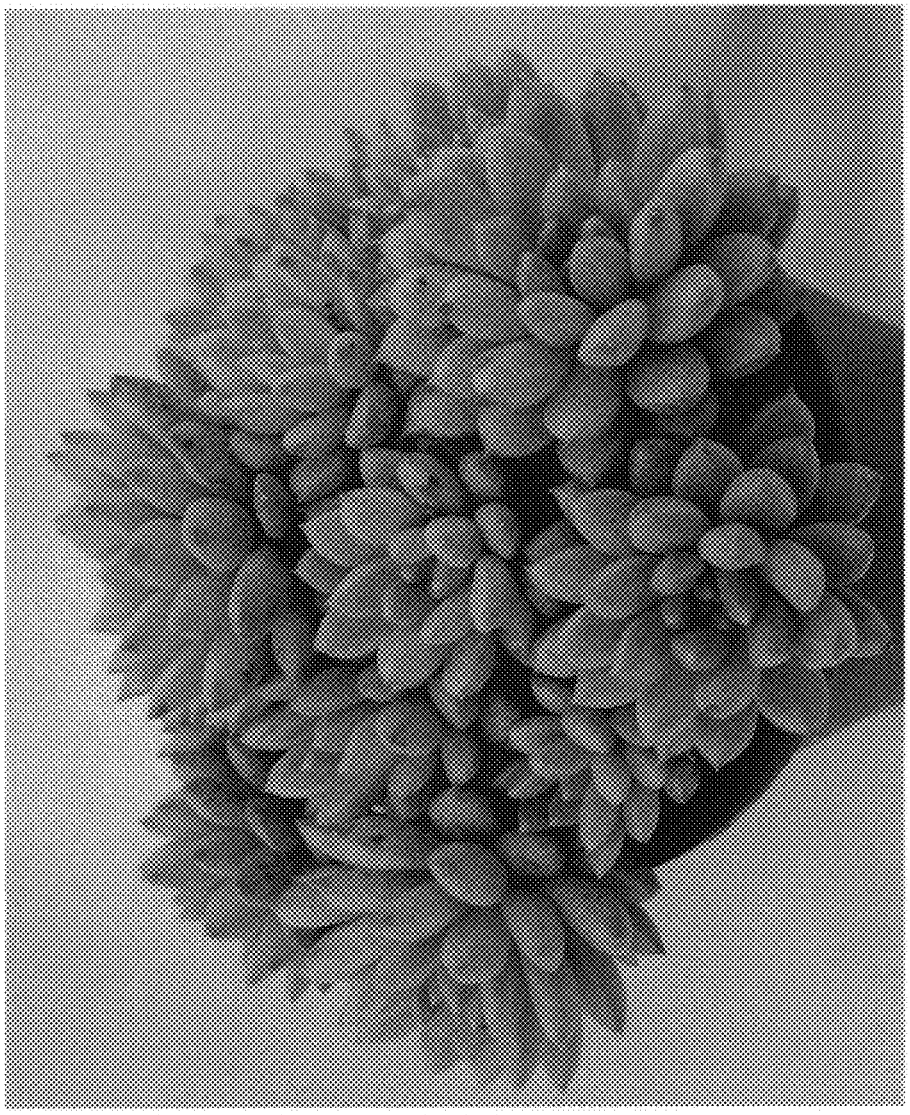

* * * * *